US010736925B2

(12) United States Patent
Khuong Huu et al.

(10) Patent No.: US 10,736,925 B2
(45) Date of Patent: Aug. 11, 2020

(54) PROBIOTICS STRAINS FOR TREATING AND/OR PREVENTING DIARRHEA

(71) Applicants: LESAFFRE ET COMPAGNIE, Paris (FR); INSTITUT NATIONAL DE LA RECHERCHE AGRONOMIQUE INRA, Paris (FR); ECOLE NATIONALE SUPERIEURE DES SCIENCES AGRONOMIQUES DE BORDEAUX AQUITAINE, Gradignan (FR)

(72) Inventors: Marie Khuong Huu, Bayonne (FR); Jean Fioramonti, Roquette (FR); Maria Urdaci, Gradignan (FR)

(73) Assignees: LESAFFRE ET COMPAGNIE, Paris (FR); INSTITUT NATIONAL DE LA RECHERCHE AGRONOMIQUE INRA, Paris (FR); ECOLE NATIONALE SUPERIEURE DES SCIENCES AGRONOMIQUES DE BORDEAUX AQUITAINE (BORDEAUX SCIENCES AGRO), Gradignan (FR)

(*) Notice: Subject to any disclaimer, the term of this patent is extended or adjusted under 35 U.S.C. 154(b) by 0 days.

(21) Appl. No.: 16/156,576

(22) Filed: Oct. 10, 2018

(65) Prior Publication Data
US 2019/0038681 A1 Feb. 7, 2019

Related U.S. Application Data

(62) Division of application No. 14/649,763, filed as application No. PCT/FR2013/053044 on Dec. 12, 2013, now abandoned.

(30) Foreign Application Priority Data

Dec. 12, 2012 (FR) .................................... 12 61916

(51) Int. Cl.
| | |
|---|---|
| *A61K 35/742* | (2015.01) |
| *G01N 33/50* | (2006.01) |
| *G01N 33/569* | (2006.01) |
| *C12R 1/125* | (2006.01) |
| *G01N 33/68* | (2006.01) |
| *A61K 35/00* | (2006.01) |

(52) U.S. Cl.
CPC ............ *A61K 35/742* (2013.01); *C12R 1/125* (2013.01); *G01N 33/5044* (2013.01); *G01N 33/56911* (2013.01); *G01N 33/6893* (2013.01); *A61K 2035/115* (2013.01); *G01N 2333/705* (2013.01); *G01N 2500/10* (2013.01)

(58) Field of Classification Search
None
See application file for complete search history.

(56) References Cited

U.S. PATENT DOCUMENTS

2008/0057047 A1 3/2008 Sas et al.

FOREIGN PATENT DOCUMENTS

| FR | 2837835 A1 * | 10/2003 | ........... A61K 39/105 |
| WO | 2007/064741 A2 | 6/2007 | |

OTHER PUBLICATIONS

Stein (molecular Microbiology reviews (2005) vol. 56, pp. 845-857).*
Calaway (Short Sharp Science (Jun. 10, 2008) p. 1.*
Kurtzman (Topics in Current Genetics (2005) pp. 29-46).*
Kim ( J Korean Med Sci (2001) vol. 16, pp. 742-744).*
Sachdev (Journal of Pediatric Gastroenterology and Nutrition (1993) vol. 13, pp. 33-38).*
EPO of FR2837835 (http://translationportal.epo.org/emtp/translate?ACTION=description-retrieval&COUNTRY=FR&ENGINE=google&FORMAT=docdb&KIND=A1&LOCALE=en_EP&NUMBER=2837835&OPS=ops.epo.org%2F3.2&SRCLANG=fr&TRGLANG=en&apikey=TSMqTfrVAvNtryGl8Qlfbozj8DnAGlqJ&PDF=vGcgfViHwGj2iP3zpTl8M7v0eNbFKCciqqivl3mvqklnapH9lj-9XJZDqA.*
Elise Heuvelin, et al., A Bifidobacterium Probiotic Strain and Its Soluble Factors Alleviate Chloride Secretion by Human Intestinal Epithelial Cells, The Journal of Nutrition (Jan. 2010) 140(1):7-11.
Pawal R. Kiela, et al., Molecular mechanism of rat NHE3 gene promoter regulation by sodium butyrate, American Journal of Physiology—Cell Physiology (Jul. 2007) 293(1):C64-C74.
George T. MacFarlane, et al., Probiotics, infection and immunity, Current Opinion on Infectious Diseases, Current Sciences (Jan. 2002) 15(5):501-506.
Geetu Raheja, et al., Lactobacillus acidophilus stimulates the expression of SLC26A3 via a transcriptional mechanism, American Journal of Physiology Gastrointestinal and Liver Physiology (Mar. 2010) 298(3):G395-G401.
Silvia Resta-Lenert, et al., Probiotics and Commensals Reverse TNF-α- and IFN-γ-Induced Dysfunction in Human Intestinal Epithelial Cells, Gastroenterology (Mar. 2006) 130(3):731-746.
Alan BR Thomson, et al., Recent advances in small bowel diseases: Part I, World Journal of Gastroenterology (Jan. 2012) 18(26):1007-9327.
Gabriel, Science (2004) vol. 266, pp. 107.
Al-Awqati, Journal of Clinical Investigation (2002) vol. 110, pp. 1599-1601.
Bacillus: http://www.bacterio.net/bacillus.html, downloaded Mar. 16, 2017.
Calaway, Short Sharp Science (Jun. 10, 2008).
Swiatecka-Urban, American Journal of Physiology (2006) vol. 290 pp. C862-C872.

(Continued)

*Primary Examiner* — Steven Pohnert
(74) *Attorney, Agent, or Firm* — Duane Morris LLP; Thomas K. Kowalski; Deborah L. Lu (57) ABSTRACT

The present invention relates to a method of selecting or identifying probiotic strains capable of acting on the absorption of water in the colon, and use thereof as medicinal products in the treatment and/or prevention of diarrhea. The invention relates in particular to the strain of *Bacillus subtilis* CU1 for use in the treatment and/or prevention of diarrhea.

3 Claims, 3 Drawing Sheets

(56) References Cited

OTHER PUBLICATIONS

Resta-Lenert, Gasteroenterology (2006) vol. 130, pp. 731-746.
Resta-Lenert, Molecular Structure and Function of the Tight Junction, Ann. N.Y. Acad. Sci. (2009) 1165: 175-182.
Thiagarajah, Current Opinion in Pharamacology (2003) vol. 3, pp. 594-599.
Urdaci, J Clin Gastroenterol (2004) vol. 38, pp. s86-s90.
CDC Pathogens causing US foodborne illnesses (Jan. 2012).

\* cited by examiner

PROBIOTICS STRAINS FOR TREATING AND/OR PREVENTING DIARRHEA

RELATED PATENT APPLICATIONS

The present patent application is a divisional of U.S. application Ser. No. 14/649,763 filed Jun. 4, 2015, which was filed pursuant to 35 U.S.C. § 371 as a U.S. National Phase application of International Patent Application No. PCT/FR2013/053044, which was filed on Dec. 12, 2013, claiming the benefit of priority to French patent application number FR 12 61916 filed on Dec. 12, 2012. The International Application was published as WO 2014/091160 on Jun. 19, 2014. The content of each of the aforementioned patent applications is incorporated by reference in its entirety.

FIELD OF THE INVENTION

The present invention relates to the field of probiotic strains, in particular probiotic strains of Bacillus, for use in the treatment and/or prevention of diarrhea. The invention also relates to a method of selecting probiotic strains that have the particular feature of acting on the absorption of water in the colon.

BACKGROUND OF THE INVENTION

When functioning normally, the human colon absorbs about 99% of the water entering its lumen, which represents about 2 liters of water per day. The colon has the capacity to absorb up to an additional 4 liters of water. However, above 6 liters of water per day, its capacity for absorption is saturated, and diarrhea develops.

Diarrhea is a common problem (worldwide, about two billion cases each year) which is characterized by stools of liquid or soft consistency, more bulky and frequent than usual (more than 3 bowel movements per day). In extreme cases, more than 20 liters of fluid can be lost per day.

Diarrhea is not a disease, but a symptom. Its commonest cause is ingestion of contaminated water or food; in that case it lasts one or two days without requiring treatment. However, diarrhea itself can cause dehydration that can prove fatal, especially in an infant, where a weight loss exceeding 10% is a hospital emergency. According to the World Health Organization, diarrhea is the second commonest cause of infant mortality in third world countries, and is responsible for 18% of deaths of children under 5 years (Bryce et al., Lancet, 2005, 365: 1147-1152).

Dehydration caused by diarrhea occurs when the losses of fluid are not compensated. In the normal situation, it is in the colon that water is removed from the stool. The phenomena of reabsorption of the water contained in ingested matter occur at the level of the colonic cells by a combination of active and passive transport of water and electrolytes. At the level of the crypts of the invaginations of the colonic epithelium, there is secretion of water from the blood to the external environment. These two phenomena compensate one another in a person in good health and are able to maintain appropriate hydration of the stool, which promotes intestinal transit and improves the conditions of circulation of the molecules.

There are many possible causes of diarrhea, including diarrhea of infectious origin induced by a viral, bacterial or parasitic pathogen and noninfectious diarrhea, such as diarrhea induced by food intolerance, a fatty diet, alcohol, a psychological factor, administration of a medicinal product, administration of a therapeutic procedure, diarrhea associated with a disease or with a clinical condition, or diarrhea associated with drug withdrawal.

Depending on the duration of the symptoms, a distinction is made between acute diarrhea and chronic diarrhea, the symptoms of which last less than two weeks and at least two weeks, respectively.

A classical medication for the treatment of diarrhea is for example loperamide, which acts both by stimulating the absorption of water and electrolytes, and by slowing the transit time. However, slowing of the transit time can be problematic in severe infections of the Salmonella, Shigella or Clostridium difficile type, since the pathogenic bacterium remains in the intestine for a long time.

Probiotics represent an interesting alternative in the treatment and/or prevention of diarrhea. The probiotics most used for this indication are the lactic bacteria. The probiotics are then generally described as having a beneficial action on the immune system and on the equilibrium of the intestinal flora.

Other studies have tried to identify new targets for the treatment or prevention of diarrhea. Thus, document WO 2004/028480 describes compounds of the thiazolidinone type for lowering the effectiveness of transport of chloride ions by the CFTR protein (Cystic Fibrosis Transmembrane Conductance Regulator) and use thereof in the treatment of secretory diarrhea. Bradford et al. (Am. J. Physiol. Gastrointes. Liver Physiol., 2009, 296: G886-G898) have examined means for treating problems of intestinal obstruction and dehydration in patients with mucoviscidosis (in which there is altered expression of CFTR).

Moreover, it has been described that the partial or complete loss of the NHE3 protein (Sodium Hydrogen Exchanger 3) in mice with mucoviscidosis reduced the incidence of intestinal obstructions, notably by increasing intestinal fluidity, and it was concluded that NHE3 is a potential target for regulating the fluidity of the intestinal tract in patients with mucoviscidosis and with altered expression of CFTR.

Therefore, there is still a need for new strategies for treating and/or preventing diarrhea.

SUMMARY OF THE INVENTION

In general, the present invention is based on the finding that, in a quite original manner, certain probiotic strains are capable of acting directly on diarrhea, by inducing absorption of water present in excess in the colon. Surprisingly and unexpectedly, the inventors showed that certain probiotic strains are capable of inhibiting the expression of transporters involved in the secretion of water in the colon and/or of stimulating the expression of transporters involved in the absorption of water in the colon, and can be used for treating and/or preventing diarrhea.

Thus, in a quite original manner, these probiotic strains do not act as inhibitors of the transporters, i.e. do not act by binding to the transporters, thus hampering their functioning, but act on their expression and therefore on the number of transporters present.

Moreover, as these probiotic strains act directly on the absorption of water present in excess in the colon, they have the advantage that they can be used for preventing and/or treating any type of diarrhea, in particular regardless of whether the diarrhea is of infectious or noninfectious origin and in the presence or absence of a dysbiosis.

The present invention thus relates to a method of selecting a probiotic strain for treating and/or preventing diarrhea, said method comprising the steps of:
measuring the effect of at least one test strain on the expression of at least one transporter involved in the absorption or secretion of water in the colon, and
selecting at least one strain that induces a decrease in the expression of at least one transporter involved in the secretion of water in the colon and/or an increase in at least one transporter involved in the absorption of water in the colon.

More specifically, in a first aspect, the present invention relates to a method of selecting a probiotic strain for treating and/or preventing diarrhea, said method comprising the steps of:
measuring the effect of at least one test strain on expression of the CFTR protein (Cystic Fibrosis Transmembrane Conductance Regulator) and/or on expression of the NHE3 protein (Sodium Hydrogen Exchanger 3), and
selecting at least one strain that induces a decrease in expression of the CFTR protein and/or an increase in expression of the NHE3 protein.

In certain embodiments, the test strain is a yeast strain or a bacterial strain. In particular, a bacterial strain to be tested can be a strain of *Bacillus*, preferably a strain of *Bacillus subtilis*.

In certain embodiments, expression of the CFTR protein and/or of the NHE3 protein is measured by electrophoresis, Western blot, immunoassay, immunohistochemistry, immunocytochemistry, mass spectrometry, RT-PCR or Northern blot.

In another aspect, the present invention relates to a probiotic strain selected using a method according to the invention, for use in the treatment and/or prevention of diarrhea.

In certain embodiments, the probiotic strain is a strain of *Bacillus subtilis*, preferably the strain of *Bacillus subtilis* CU1 deposited at the CNCM (Collection Nationale de Cultures de Microorganismes/National Collection of Cultures of Microorganisms, 25 rue du Docteur Roux, 75724 Paris Cedex 15) on Oct. 25, 2001 under number 1-2745.

In a subsidiary aspect, the present invention relates to cells obtained by culture of a probiotic strain selected using a method according to the invention, to be used in the treatment and/or prevention of diarrhea.

In particular, the invention relates to cells of *Bacillus subtilis* obtained by culture of the strain of *Bacillus subtilis* CU1 deposited at the CNCM on Oct. 25, 2001 under number 1-2745, for use in the treatment and/or prevention of diarrhea.

The present invention also relates to a method of treating and/or preventing diarrhea in a patient comprising administration, to the patient, of an effective amount of cells obtained by culture of a probiotic strain selected using a method according to the invention.

In certain embodiments, the method of treating and/or preventing diarrhea comprises administration of cells of *Bacillus subtilis* obtained by culture of a probiotic strain of *Bacillus subtilis*, preferably the strain of *Bacillus subtilis* CU1 deposited at the CNCM on Oct. 25, 2001, under number 1-2745.

In another aspect, the present invention relates to a composition for use in the treatment and/or prevention of diarrhea, said composition comprising at least one probiotic strain according to the invention, or cells obtained by culture of said strain. In particular, the composition comprises cells of *Bacillus subtilis* obtained by culture of the strain of *Bacillus subtilis* CU1 deposited at the CNCM on Oct. 25, 2001, under number 1-2745.

The forms of diarrhea that can be treated prophylactically and/or therapeutically according to the invention include acute diarrhea and chronic diarrhea.

In certain embodiments, the diarrhea treated according to the invention is diarrhea of infectious origin that is induced by a viral, bacterial or parasitic pathogen.

In other embodiments, the diarrhea treated according to the invention is diarrhea of noninfectious origin.

Diarrhea of noninfectious origin is for example diarrhea induced by a food intolerance, diarrhea induced by a fatty diet, diarrhea induced by alcohol, diarrhea induced by a psychological factor, diarrhea induced by the administration of a medicinal product, diarrhea induced by the administration of a therapeutic procedure, diarrhea associated with a disease or with a clinical condition, or diarrhea associated with drug withdrawal.

A more detailed description of certain preferred embodiments of the invention is given below.

DETAILED DESCRIPTION OF THE INVENTION

As mentioned above, the present invention relates to the identification of probiotic strains capable of acting on the absorption of water in the colon by direct action at the level of the transporters involved in the regulation of the intestinal fluid, and their use as medicinal products in the treatment and/or prevention of diarrhea.

I—Method of Selecting Probiotic Strains

A method of selection according to the invention has the goal of identifying a probiotic strain that is useful in the treatment and/or prevention of diarrhea.

The present invention thus relates to a method of selecting a probiotic strain for treating and/or preventing diarrhea, said method comprising the steps of:
  measuring the effect of at least one test strain on the expression of at least one transporter involved in the absorption or secretion of water in the colon, and
  selecting at least one strain that induces a decrease in the expression of at least one transporter involved in the secretion of water in the colon and/or an increase in the expression of at least one transporter involved in the absorption of water in the colon.

An example of transporter involved in the secretion of water in the colon is the CFTR protein (Cystic Fibrosis Transmembrane Conductance Regulator).

An example of transporter involved in the absorption of water in the colon is the NHE3 protein (Sodium Hydrogen Exchanger 3).

A preferred method according to the invention is characterized in that it comprises steps of:
  measuring the effect of at least one test strain on the expression of the CFTR protein and/or on the expression of the NHE3 protein, and
  selecting at least one strain that induces a decrease in the expression of the CFTR protein and/or an increase in the expression of the NHE3 protein.

The strain selected as a result of the method according to the invention is thus a probiotic strain useful in the treatment and/or prevention of diarrhea.

"Probiotic strain" is herein intended to denote a strain of a live microorganism that exerts a beneficial effect on the health of the host.

The host is generally a human being, but it is conceivable that the host can be another mammal, for example dogs, cats, ruminants, especially sheep, goats, calves, cows, cervids, camelids, equines, Old-World swine, in particular pigs and piglets, leporids, murids, and rodents of the Caviidae family.

Test Strains

The strain to be tested using a method according to the invention may be any strain of microorganism.

In certain embodiments, the test strain is a yeast strain. Among the yeasts that can be tested, one can mention, for example, the yeasts of the genus *Saccharomyces*, in particular the species *Saccharomyces boulardii*, *Saccharomyces cerevisiae*, the yeasts of the genus *Kluyveromyces*, in particular the species *Kluyveromyces marxianus*.

In other embodiments, the strain to be tested is a bacterial strain.

The test strain is preferably selected from the bacteria recognized as being harmless to humans and/or animals.

Among the bacteria that can be tested, one can mention, for example, the bacteria of the genus *Bifidobacterium*, in particular the species *Bifidobacterium animalis*, *Bifidobacterium bifidum*, *Bifidobacterium infantis*, *Bifidobacterium lactis*, *Bifidobacterium longum*, and *Bifidobacterium breve*; the bacteria of the genus *Lactobacillus*, in particular the species *Lactobacillus reuteri*, *Lactobacillus acidophilus*, *Lactobacillus bulgaricus*, *Lactobacillus brevis*, *Lactobacillus casei*, *Lactobacillus helveticus*, *Lactobacillus johnsonii*, *Lactobacillus plantarum*, *Lactobacillus paracasei*, *Lactobacillus rhamnosus*, and *Lactobacillus salivarius*; the bacteria of the genus *Weisella*, in particular the species *Weisella cibaria*, *Weisella kimchii*, *Weisella thailandensis*; the bacteria of the genus *Bacillus*, in particular the species *Bacillus subtilis*, *Bacillus coagulans*, *Bacillus amyloliquefaciens*, *Bacillus licheniformis*, *Bacillus cereus* and *Bacillus clausii*; the bacteria of the genus *Lactococcus*, in particular the species *Lactococcus lactis*; the bacteria of the genus *Enterococcus*, in particular the species *Enterococcus faecium*, *Enterococcus fecalis*; the bacteria of the genus *Streptococcus*, in particular the species *Streptococcus thermophilus*; the bacteria of the genus *Escherichia*, in particular the species *Escherichia coli*.

Expression of CFTR and/or NHE3

A method according to the invention comprises measuring the effect of the test strain on the expression of at least one transporter involved in the absorption or secretion of water in the colon, in particular on expression of the CFTR protein and/or of the NHE3 protein.

As used herein, "CFTR protein" means the protein which in the human species is encoded by the gene CFTR (for "Cystic Fibrosis Transmembrane Conductance Regulator"), which is located on locus 7q31.2, in region q31.2 of the long arm of chromosome 7. The CFTR gene is highly conserved among species. In the human being, the CFTR protein has for example the polypeptide sequence with the GenBank accession number NP 00483, which is 1480 amino acid long.

The CFTR protein forms a channel that is permeable to the chloride and thiocyanate ions of the epithelial cells.

The CFTR protein is expressed at the apical pole of the epithelial cells of the pancreatic and biliary ducts, of the intestinal crypts, of the tracheo-bronchial tree, of the renal tubules, of the genital system and of the sweat glands.

It has been demonstrated that inhibitors of CFTR, such as thiazolidinone, have found application in the treatment and/or prevention of diarrhea (Verkman et al., Curr. Pharm. Des., 2006, 12: 2235-2247).

In a method of selection according to the invention, a test strain that induces a decrease in expression of the protein CFTR can therefore be useful in the treatment and/or prevention of diarrhea.

As used herein, "NHE3 protein" means the protein which, in the human species, is encoded by the NHE3 gene (for "Sodium-Hydrogen Exchanger 3", also known by the name SLC9A3 for "Solute Carrier Family 9 Member 3"), which is located on chromosome 13. In humans, the NHE3 protein has for example the polypeptide sequence with the GenBank accession number NP 004165, which is 834 amino acid long.

The NHE3 protein is expressed in the nephron of the kidney and in the apical membrane of the endothelial cells of the intestine, where it is mainly responsible for maintaining the sodium balance.

It has been shown that mice genetically modified to inactivate the NHE3 gene suffered from diarrhea (Schultheis et al., 1998, Nat. Genet 19: 282-285).

In a method of selection according to the invention, a test strain that induces an increase in expression of the NHE3 protein may therefore be useful in the treatment and/or prevention of diarrhea.

In the context of the present invention, measurement of the effect of the test strain on the expression of a transporter involved in the absorption or secretion of water in the colon, in particular on expression of the CFTR protein and/or of the NHE3 protein, can be carried out using any method known by a person skilled in the art (see for example, Harlow and Lane, "*Antibodies: A Laboratory Manual*", 1988, Cold Spring Harbor Laboratory: Cold Spring Harbor, N.Y.), since the nature of the method used is not a critical or limiting element.

In general, the expression level of a protein can be determined by a direct method, such as by a method of electrophoresis, a method of Western blot, a method of immunoassay, a method of immunohistochemistry, a method of immunocytochemistry, or a method of mass spectrometry.

It is also possible to determine the expression level of a protein by an indirect method.

An indirect method can consist of measuring the transcription level of the corresponding gene, for example by RT-PCR (reverse transcription followed by polymerase chain reaction), preferably by quantitative RT-PCR, or by a method of Northern blot.

Another example of an indirect method is a method which consists of measuring the activity of the protein, the activity of the protein being correlated with the amount of functional protein present.

In certain preferred embodiments, the expression level of the transporter, and in particular of the CFTR protein and/or of the NHE3 protein, is determined by electrophoresis.

Electrophoresis allowed proteins to be separated according to their molecular weight. Electrophoresis on polyacrylamide gel containing sodium lauryl sulfate (called SDS-PAGE for Sodium Dodecyl Sulfate PolyAcrylamide Gel Electrophoresis) is generally used. It can also be two-dimensional electrophoresis, such as isoelectric focusing, with which it is possible to separate the proteins according to their molecular weight and their isoelectric point.

In certain embodiments of the invention, the expression level of the transporter, and in particular of the CFTR protein and/or of the NHE3 protein, is determined by Western blot.

Western blot, also called Western technique, consists of separating the proteins by polyacrylamide gel electrophoresis, and then transferring the proteins from the polyacrylamide gel to a supporting membrane, on which the proteins of interest are detected using labeled antibodies that are specific to said proteins.

In certain preferred embodiments, the expression level of the transporter, and in particular of the CFTR protein and/or of the NHE3 protein, is determined by an immunoassay. As used herein, "immunoassay" means any technique that uses the antigen-antibody reaction for detecting and quantifying antigens, antibodies or similar substances. An antibody-antigen complex can be visualized in several ways. In most cases, an antibody is conjugated to an enzyme (e.g. peroxidase) that can catalyze a reaction producing color (e.g. immunoperoxidase staining). Alternatively, the antibodies can be labeled with a fluorophore (e.g. FITC, Rhodamine, Tex. Red or Alexa Fluor). The antibody-antigen complex is then detected by immunofluorescence.

Monoclonal antibodies specific to the human CFTR protein and the human NHE3 protein are known in the art and are commercially available.

In certain embodiments of the invention, the expression level of the transporter, and in particular of the CFTR protein and/or of the NHE3 protein is determined by immunohistochemistry. The term "immunohistochemistry" refers to a method based on the use of antibodies for locating a protein in tissues. The tissue is generally fixed, washed, and then permeabilized. It is then incubated with a primary antibody that specifically recognizes the protein of interest (here, for example, the CFTR protein or the NHE3 protein). A second antibody coupled to a detection system is added. The detection system is for example a fluorochrome or an enzyme which, when put in the presence of the substrate, causes a colored reaction. This second antibody recognizes the constant part Fc of the primary antibody and must be derived from a species other than the species of primary antibody. After mounting in a medium protecting the fluorescence of the sample if it is a fluorochrome or in the presence of the substrate if it is an enzyme, the tissue is analyzed using the fluorescence or confocal microscope. The expression level of the protein of interest can then be determined by densitometry, by measuring the fluorescence intensity, or by spectrophotometry.

In certain embodiments of the invention, the expression level of the transporter, and in particular of the CFTR protein and/or of the NHE3 protein is determined by immunocytochemistry.

Immunocytochemistry is a technique similar to immunohistochemistry, except that the starting sample is a cytological preparation instead of a tissue.

In certain embodiments of the invention, the expression level of the transporter, and in particular of the CFTR protein and/or of the NHE3 protein is determined by mass spectrometry.

In certain embodiments of the invention, the expression level of the transporter, and in particular of the CFTR protein and/or of the NHE3 protein is determined by RT-PCR.

RT-PCR consists of reverse transcription of RNA to cDNA, followed by a polymerase chain reaction (PCR). RT-PCR is preferably a quantitative RT-PCR which makes it possible to quantify the initial RNA corresponding to the protein of interest.

In certain embodiments of the invention, the expression level of the transporter, and in particular of the CFTR protein and/or of the NHE3 protein, is determined by Northern blot.

Northern blot, also called Northern transfer, is a technique consisting of separating the RNA according to size by gel electrophoresis, then transferring the RNA from the gel onto a membrane where it can be detected with a labeled hybridization probe that is specific to the RNA of the protein to be quantified.

Biological Sample

One method according to the invention comprises measuring the effect of the test strain on the expression of at least one transporter involved in the absorption or secretion of water in the colon, in particular on expression of the CFTR protein and/or of the NHE3 protein, in a biological sample.

The term "biological sample", as used herein, is used in its broadest sense. A biological sample can be any biological tissue in which the protein of interest (in particular the CFTR protein or the NHE3 protein) is expressed and can therefore be detected and quantified.

The biological samples that can be used when applying a method of selection according to the invention can be, for example, samples from the intestine, the pancreatic ducts, the bile ducts, the renal tubules, the tracheo-bronchial tree, the genital system, the sweat glands and the nephron of the kidney.

In certain preferred embodiments, the biological sample is a sample from the intestine, preferably a sample from the colon.

A tissue sample is preferably taken from a model animal, for example by biopsy. The model animal is preferably a mammal, for example a mouse, a rat, a rabbit, a pig, a chicken, a monkey. The model animal can be a transgenic animal.

A preferred biological sample according to the invention is a tissue sample comprising colonocytes, i.e. cells from the colonic mucosa.

The biological sample can also be biological material derived from a tissue and which expresses the protein of interest.

The derived biological material is for example selected from cells isolated from the tissue sample or from proteins extracted from cells isolated from the tissue sample.

The term "biological sample" also includes cells of a cell line known to express the protein of interest, in particular the CFTR protein and/or the NHE3 protein.

Examples of cell lines expressing the CFTR protein include the Caco-2 cells isolated from the colon, the HT-29 cells isolated from the colon or T84 cells isolated from the colon.

Examples of cell lines expressing the NHE3 protein include Caco-2 cells isolated from the colon, HT-29 cells isolated from the colon or T84 cells isolated from the colon.

These cell lines are commercially available, for example from the ATCC (American Type Culture Collection).

In certain embodiments, the biological sample is a protein extract isolated from cells or from tissues expressing the protein of interest, in particular the CFTR and/or NHE3 protein. The methods of extracting proteins are well known by a person skilled in the art (see for example, "*Protein Methods*", D. M. Bollag et al., 2$^{nd}$ Ed., 1996, Wiley-Liss; "*Protein Purification Methods: A Practical Approach*", E. L. Harris and S. Angal (Eds.), 1989; "*Protein Purification Techniques: A Practical Approach*", S. Roe, 2$^{nd}$ Ed., 2001, Oxford University Press; "*Principles and Reactions of Protein Extraction, Purification, and Characterization*", H. Ahmed, 2005, CRC Press: Boca Raton, Fla.). There are also commercial kits for extracting proteins from tissues or from biological fluids. Such kits are, for example, sold by BioRad Laboratories (Hercules, Calif.), BD Biosciences Clontech (Mountain View, Calif.), Chemicon International, Inc. (Temecula, Calif.), Calbiochem (San Diego, Calif.), Pierce Biotechnology (Rockford, Ill.), and Invitrogen Corp. (Carlsbad, Calif.). A person skilled in the art knows how to select the kit that is the most suitable for the situation.

Effect of the Test Strain

In a method according to the invention, the effect of the test strain on the expression of a transporter involved in the absorption or secretion of water in the colon, in particular of the CFTR protein and/or of the NHE3 protein, is determined by comparing the expression level of the protein of interest measured in a biological sample obtained from a model animal that has been treated with the test strain and the expression level of the protein of interest measured in a biological sample (of the same kind) obtained from a model animal (of the same kind) that has not been treated with the test strain. This last-mentioned animal is called the control animal.

Thus, for example, when applying a method according to the invention in which the biological sample comes from a model animal, a given quantity of cells obtained by culture of the test strain is administered to the model animal.

The quantity of cells can be administered on one occasion.

Alternatively, the quantity of cells can be administered several times, either on the same day or over several days or weeks.

The cells obtained by culture of the test strain can be administered by any method of administration suitable for the model animal used. For example, administration can be carried out by injection, in particular by intragastric injection, of a solution or of a suspension containing a suitable vehicle and a given quantity of cells obtained by culture of the test strain. The same volume of a solution containing only the vehicle is administered to the control animal.

Moreover, when applying a method according to the invention in which the biological sample is a cell line, the effect of the test strain is determined by comparing the expression level of the protein of interest measured on the cells of the cell line that were treated with the test strain and the expression level of the protein of interest measured in cells (of the same cell line) that have not been treated with the test strain. These last-mentioned cells are called control cells.

Thus, for example, when applying a method according to the invention in which the biological sample is a cell line, cells of a cell line are incubated with a given quantity of a solution or of a suspension containing a suitable vehicle and a given quantity of cells obtained by culture of the test strain. The control cells of the cell line are incubated in the same conditions in the presence of the same volume of a solution containing only the vehicle.

The methods of culture of a strain, whether it is a yeast strain or a bacterial strain, are known in the art, and a person skilled in the art knows how to optimize the culture conditions for each strain in relation to its nature.

Moreover, a person skilled in the art knows how to determine the optimum quantities of cells obtained by culture of the test strain for administration to a model animal or for incubating with cells of a cell line.

For example, *Bacillus subtilis* cells are obtained by culture of a strain of *Bacillus subtilis* in a culture medium, in particular as described in the book Biotechnology, 5th edition, R. Scriban, Edition Tec. & Doc., 1999, ISBN: 2-7430-0309-X.

Typically, a method of producing cells of *Bacillus subtilis* by culture of a strain of *Bacillus subtilis* comprises the steps of:

seeding a culture medium with an inoculum of the strain of *Bacillus subtilis*, culturing in aerobic conditions, to obtain multiplication of the cells, separating the biomass from its culture medium, to obtain cells of *Bacillus subtilis*.

The cells of *Bacillus subtilis* thus obtained are predominantly in the vegetative form.

The expression "predominantly in the vegetative form" signifies that at least 70% of the cells are in the vegetative form, preferably at least 80%, and more preferably at least 90%.

The "vegetative form" of a bacterium denotes the form of a bacterium placed in favorable conditions.

An example of favorable conditions is a nonlimiting culture medium at a temperature and a pH favorable for bacterial multiplication.

A nonlimiting culture medium contains all the nutrients necessary for multiplication of the cells.

The method of producing cells of *Bacillus subtilis* can also comprise an intermediate step of placing the cells in unfavorable conditions, between the step of culturing in aerobic conditions and the step of separating the biomass. The cells of *Bacillus subtilis* obtained at the end of the method of production are thus predominantly in sporulated form.

The expression "predominantly in sporulated form" signifies that at least 70% of the cells are in sporulated form, preferably at least 80%, and more preferably at least 90%.

The "sporulated form" of a bacterium denotes the form of a bacterium placed in unfavorable conditions. The sporulated form is thus a form of resistance that enables it to resist a difficult environment, such as for example a lack of nutrients, i.e. a limiting nutrient medium, water stress, wide variation of pH or temperature, or passage through the alimentary canal.

Placing the cells of bacteria in unfavorable conditions is for example obtained by: not renewing the culture medium of the bacteria, stopping feed to the culture medium, using a limiting culture medium, a change of temperature, a change of pH or a combination thereof.

The method of production of cells of *Bacillus subtilis* can also comprise a further step of drying the cells, to obtain cells of *Bacillus subtilis* in dry form.

The expression "cells of *Bacillus subtilis* in dry form" means that the biomass obtained at the end of the method of production of the cells of *Bacillus subtilis* comprises more than 90% of dry matter, preferably more than 95% of dry matter.

The drying is for example drying by lyophilization, fluidized bed drying or spray-drying.

Identification of a Probiotic Strain for Treating and/or Preventing Diarrhea

By comparing the expression level of the protein of interest measured in the sample treated with the test strain and the expression level of the protein of interest measured in the control sample, it is possible to determine whether the strain tested induces a decrease or an increase in expression of the protein of interest or whether it has no effect on said expression.

As noted above, a strain for which it has been determined by a method of selection according to the invention that it induces a decrease in the expression of at least one transporter involved in the secretion of water in the colon and/or an increase in the expression of at least one transporter involved in the absorption of water in the colon is a probiotic strain that may be useful in the treatment and/or prevention of diarrhea.

The inventors have demonstrated that such a probiotic strain is capable of inducing absorption of water present in excess in the colon, and therefore finds application in the treatment and/or prevention of diarrhea.

"Decrease in the expression of a transporter involved in the secretion of water in the colon" is intended to denote a significant decrease in the expression of said transporter relative to its expression in the absence of the test strain.

The "significant" character of this decrease is determined by statistical analysis.

When the effect on expression of the transporter is measured by immunohistochemistry, a "decrease in expression of the transporter" corresponds to a significant decrease in fluorescence intensity/$\mu m^2$ corresponding to the expression of said transporter relative to that in the absence of the test strain.

"Increase in expression of a transporter involved in the absorption of water in the colon" is intended to denote a significant increase in the expression of said transporter relative to its expression in the absence of the test strain.

The "significant" character of this increase is determined by statistical analysis.

When the effect on expression of the transporter is measured by immunohistochemistry, an "increase in expression of the transporter" corresponds to a significant increase in fluorescence intensity/$\mu m2$ corresponding to expression of said transporter relative to that in the absence of the test strain.

As a person skilled in the art will appreciate, identification of a probiotic strain useful for treating and/or preventing diarrhea can be carried out using just one method of selection according to the invention. The method according to the invention can be carried out using a single type of biological sample, for example a given model animal, or using several types of biological samples, for example a cell line, and then at least one model animal.

Alternatively, identification of a probiotic strain capable of acting on the absorption of water in the colon can be carried out using a method of selection according to the invention and then supplementing this selection with a series of tests and clinical trials, well known by a person skilled in the art.

II—Use of a Probiotic Strain in the Treatment and/or Prevention of Diarrhea

The invention relates to any probiotic strain identified by a method according to the invention as being capable of inducing absorption of water present in excess in the colon, for use in the treatment and/or prevention of diarrhea. The invention also relates to such a probiotic strain for use in the manufacture of a medicinal product for treating and/or preventing diarrhea.

As noted above, the probiotic strain can be any strain of microorganism, in particular a yeast strain or a bacterial strain, such as those mentioned above.

In particular, the inventors have demonstrated that the strain of *Bacillus subtilis* CU1 deposited at the CNCM on Oct. 25, 2001 under number 1-2745 is a probiotic strain that acts on the absorption of excess water in the colon, and can therefore be useful for treating and/or preventing diarrhea.

This strain was described in document FR 2 837 835, which discloses a live adjuvant comprising said strain for immunization at the level of the gastrointestinal mucosa.

The invention also relates to all yeast cells or bacterial cells obtained by culture of a probiotic strain identified by a method according to the invention for use in the treatment and/or prevention of diarrhea.

As pointed out above, the culture conditions of a strain are generally known in the art or can easily be determined by a person skilled in the art.

In particular, the invention relates to cells obtained by culture of the strain of *Bacillus subtilis* CU1 deposited at the CNCM on Oct. 25, 2001 under number 1-2745, for use in the treatment and/or prevention of diarrhea.

The "cells obtained by culture of the strain of *Bacillus subtilis* CU1 deposited at the CNCM on Oct. 25, 2001 under number 1-2745" are called "CU1 cells" hereinafter.

The production of CU1 cells can be carried out as described above.

The CU1 cells used in the treatment and/or prevention of diarrhea are cells in sporulated form and/or in vegetative form.

In a preferred embodiment, the CU1 cells are predominantly in sporulated form.

In a preferred embodiment, the CU1 cells used in the treatment and/or prevention of diarrhea are in dry form.

In a particularly advantageous embodiment of the invention, the CU1 cells used in the treatment and/or prevention of diarrhea are predominantly in sporulated form and in dry form.

The invention also relates to any probiotic yeast cell extract or probiotic bacterial cell extract and any filtrate from culture of a probiotic strain, the extract or the filtrate possessing the capacity for inducing a decrease in expression of the CFTR protein and/or an increase in expression of the NHE3 protein, and therefore being capable of inducing absorption of water in excess in the colon.

A method of treating and/or preventing diarrhea according to the invention comprises the administration, to the patient, of an effective amount of yeast cells or of bacterial cells obtained by culture of a probiotic strain identified by a method described herein. The effective amount of yeast cells or of bacterial cells, which can be administered in one or more doses, can be determined by the physician. The exact amount to administer can vary from one patient to another, depending on the patient's age, weight, and general condition, the nature and severity of the diarrhea, etc. The exact amount to administer can also vary depending on the desired therapeutic effect (i.e. for preventing diarrhea or for treating diarrhea).

The route of administration, oral or parenteral, can be selected depending on the nature of the diarrhea and/or depending on the patient's age and general condition.

In the case of prevention of diarrhea, the yeast cells or the bacterial cells obtained by culture of a probiotic strain identified by the method according to the invention are administered before the symptoms appear.

In the case of treatment of diarrhea, the yeast cells or the bacterial cells obtained by culture of a probiotic strain identified by the method according to the invention are administered after the symptoms appear.

In general, any form of diarrhea can be treated using a probiotic strain according to the invention or cells obtained by culture of said probiotic strain, including acute forms of diarrhea and chronic forms of diarrhea.

"Acute diarrhea" means diarrhea whose symptoms last less than two weeks, and "chronic diarrhea" means diarrhea whose symptoms last at least two weeks, preferably at least one month.

Acute diarrhea includes, for example, viral gastroenteritis, bacterial gastroenteritis, and food poisoning (for example salmonelloses, shigelloses, *Staphylococcus aureus* infections, *Bacillus cereus* infections, *Escherichia coli* infections).

Chronic diarrhea includes, for example, malabsorption syndrome, gastroenteropathies (coeliac disease, Whipple's disease, Crohn's disease, etc.), motor diarrhea (i.e. diarrhea due to acceleration of intestinal transit), secretory diarrhea (i.e. diarrhea due to acceleration of water-electrolyte secretion in the small intestine and/or the colon), osmotic diarrhea (i.e. diarrhea resulting from the presence, in the gastrointestinal tract, of solutes that are poorly absorbed and produce an osmotic effect).

Other diarrheas that can be treated using a probiotic strain according to the invention or cells obtained by culture of a probiotic strain according to the invention include diarrhea due to anxiety or to intense emotions, diarrhea due to food intolerance (for example, lactose in cow's milk, sorbitol, gluten, etc.), diarrhea due to certain treatments such as magnesia therapy, radiotherapy or chemotherapy or to certain forms of surgery such as gastrectomy or ileal resection, diarrhea due to an overload or irritation of the stomach, of the intestines, of the colon, etc., diarrhea due to withdrawal of drugs such as heroin, diarrhea due to certain medicines such as antibiotics.

Other examples of diarrhea that can be treated using a probiotic strain according to the invention or cells obtained by culture of a probiotic strain according to the invention, include diarrhea accompanying bilious attacks or indigestion, diarrhea resulting from the overconsumption of certain laxative foodstuffs, and runner's diarrhea.

In certain advantageous embodiments, the diarrhea treated using a probiotic strain according to the invention or cells obtained by culture of a probiotic strain according to the invention is not diarrhea induced by the administration of an antibiotic, or more generally by the administration of a medicinal product.

In other advantageous embodiments, the diarrhea treated using a probiotic strain according to the invention or cells obtained by culture of a probiotic strain according to the invention is not diarrhea of infectious origin.

III—Compositions

The present invention also relates to a composition for use in the treatment and/or prevention of diarrhea, said composition comprising at least one probiotic strain according to the invention, or more specifically cells obtained by culture of such a strain. In particular, the composition comprises an effective amount of cells obtained by culture of the strain of *Bacillus subtilis* CU1 deposited at the CNCM on Oct. 25, 2001 under number 1-2745.

The composition according to the invention can be a food composition, a food supplement or a pharmaceutical composition.

A food composition denotes any type of food, drink or confectionery.

The food composition can for example be a drink, a cereal bar, a chewing gum, chocolate, a milk product, such as a fermented milk product, a fermented product of vegetable origin.

"Food supplement" means a food product whose aim is to supplement the normal diet. A food supplement constitutes a concentrated source of nutrients or of other substances having a nutritional or physiological effect, alone or combined.

A food supplement is marketed in a dosage form, namely the dosage forms such as capsule, pastille, tablet, pill and other similar forms, sachet of powder, ampule of liquid, bottle equipped with a dropper and other similar forms of liquid or powder preparations intended to be taken in measured units of a small amount.

A composition according to the invention is for example suitable for daily use of the cells obtained by culture of the probiotic strain in an amount from $1.10^8$ CFU to $1.10^{11}$ CFU, preferably in an amount from $1.10^9$ CFU to $1.10^{10}$ CFU when it is intended for human use.

A composition according to the invention is for example suitable for daily use of the cells obtained by culture of the probiotic strain in an amount from $1.10^5$ CFU to $1.10^{11}$ CFU, preferably in an amount from $1.10^6$ CFU to $1.10^{10}$ CFU when it is intended for veterinary use.

The term CFU denotes a Colony Forming Unit.

IV—Pharmaceutical Compositions

Due to its direct action on the transporters involved in the regulation of the intestinal fluid, a probiotic strain identified by a method of the invention, or more specifically yeast cells or bacterial cells obtained by culture of such a strain, can be used as a therapeutic agent.

These yeast or bacterial cells can be administered as such or in the form of a preparation or pharmaceutical composition in the presence of at least one physiologically acceptable vehicle or excipient. In the context of the present invention, "physiologically acceptable vehicle or excipient" means any medium or additive that does not interfere with the efficacy of the biological activity of the active principle (here, the yeast or bacterial cells), and that is not excessively toxic to the patient or subject, at the concentrations at which it is administered. A physiologically acceptable vehicle or excipient can be a vehicle or excipient suitable for administration to humans and/or to animals (especially to mammals).

The pharmaceutical compositions according to the present invention can be administered using any effective combination of dosage and of route of administration for obtaining the desired therapeutic effect. The exact amount to administer can vary from one patient to another, depending on the patient's age, weight, and general condition, the nature and severity of the diarrhea, etc. The route of administration (oral or parenteral) can be selected depending on the nature of the diarrhea and/or depending on the patient's age and/or health.

As an example, the invention relates to a pharmaceutical composition as defined above for daily use of cells obtained by culture of said probiotic strain in an amount from $1.10^8$ CFU to $1.10^{11}$ CFU, preferably in an amount from $1.10^9$ CFU to $10^{10}$ CFU, when it is intended for human use.

The invention also relates to a pharmaceutical composition as defined above, for daily use of cells obtained by culture of said probiotic strain in an amount from $1.10^5$ CFU to $1.10^{11}$ CFU, preferably in an amount from $1.10^6$ CFU to $1.10^{10}$ CFU, when it is intended for veterinary use.

The formulation of a pharmaceutical composition according to the present invention can vary depending on the route of administration and dosage for which the composition is intended to be used. After formulation with at least one physiologically acceptable vehicle or excipient, a pharmaceutical composition of the invention can be in any suitable form for administration to a mammal, in particular a human, for example in the form of lozenges, tablets, sugar-coated pills, capsules, syrups, ointments, injectable solutions, suppositories, etc. A person skilled in the art knows how to select the most suitable vehicles and excipients for preparing a given type of formulation. Thus, for example, excipients such as water, 2,3-butanediol, Ringer solution, isotonic solutions of sodium chloride, synthetic mono- or diglycerides, and oleic acid are often used in the formulation of injectable preparations. Liquid compositions, including emulsions, microemulsions, solutions, suspensions, syrups, elixirs, etc., can be formulated in the presence of solvents, solubilizers, emulsifiers, oils, fatty acids, and other additives such as suspension agents, preservatives, sweeteners, flavorings, viscosity modifiers, colorants, etc. Solid compositions for administration by the oral route can be formulated in the presence of an inert excipient such as sodium citrate, and optionally additives such as binders, humectants, disintegrants, absorption accelerators, lubricants, etc.

In certain embodiments, a pharmaceutical composition according to the present invention is formulated for immediate release of the active principle or active principles, in particular the yeast cells or bacterial cells obtained by culture of the probiotic strain. Alternatively, a pharmaceutical composition can be formulated for prolonged or targeted release of the active principle or active principles or for protection of the active principle or active principles, for example against gastric acidity and enzymes.

It is thus possible to use coatings that are resistant to pH and/or to the action of the gastric enzymes, coatings sensitive to pH and/or to enzymatic action, or bioadhesive coatings that adhere to the walls of the stomach or intestine, or by using encapsulation systems.

The pharmaceutical compositions according to the present invention can, moreover, contain at least one additional active pharmaceutical ingredient (i.e. in addition to the yeast or bacterial cells obtained by culture of the probiotic strain).

"Active pharmaceutical ingredient" means any compound or substance whose administration has a therapeutic effect or a beneficial effect on the health or general condition of a patient or of a subject to which it is administered.

Thus, an active pharmaceutical ingredient can be active against diarrhea to be prevented or treated by administration of the pharmaceutical composition; can be active against a condition or a symptom associated with diarrhea (for example, fever, vomiting or abdominal cramps); or can increase the availability and/or the activity of the active principle or active principles of the pharmaceutical composition.

Examples of active pharmaceutical ingredients that can be present in a composition of the present invention include, without limitation, anti-inflammatories, antibiotics, antipyretics, antiemetics, antihistamines, vitamins, antispasmodics, etc.

In an advantageous embodiment, the other active pharmaceutical ingredient is not a strain of *Bacillus subtilis* or cells obtained by culture of such a strain, preferably is not a bacterial strain or cells obtained by culture of such a strain, more preferably is not a probiotic strain or cells obtained by culture of such a strain.

An example of pharmaceutical composition according to the present invention is a composition comprising yeast or bacterial cells obtained by culture of the probiotic strain, as the only active pharmaceutical ingredient.

In a preferred embodiment, the composition according to the invention contains cells obtained by culture of the strain of *Bacillus subtilis* CU1 deposited at the CNCM on Oct. 25, 2001 under number 1-2745, to the exclusion of any other bacterial strain.

In another preferred embodiment, the composition according to the invention contains cells obtained by culture of the strain of *Bacillus subtilis* CU1 deposited at the CNCM on Oct. 25, 2001 under number 1-2745, to the exclusion of any other bacterial or yeast strain.

In yet another preferred embodiment, the composition according to the invention contains cells obtained by culture of the strain of *Bacillus subtilis* CU1 deposited at the CNCM on Oct. 25, 2001 under number 1-2745, as the only pharmaceutical active ingredient.

Unless they are defined otherwise, all the technical and scientific terms used in the description have the same meaning as that generally understood by an ordinary specialist in the field to which this invention belongs. Moreover, all the publications, patent applications, all the patents and all other references mentioned here are incorporated by reference.

EXAMPLES

The following examples describe some embodiments of the present invention. However, it is to be understood that the examples are only presented for purposes of illustration and do not in any way limit the scope of the invention.

Example 1: Selection of Probiotic Strains Intended for Preventing and/or Treating Diarrhea Material and Methods
Probiotic Strains Tested.
The strains tested are as follows: a strain of *Lactobacillus plantarum* and the strain *Bacillus subtilis* CU1.
The cells of *Bacillus subtilis* CU1 (hereinafter CU1) are used in sporulated form and dry.
The cells of *Lactobacillus plantarum* (hereinafter LR) are used in a lyophilized, vegetative form.
Measurement of the Effect of a Probiotic Strain on Expression of CFTR and of NHE3.
Four mice were treated for 2 weeks, each with $10^9$ CFU/day of CU1.
Four mice were treated for 2 weeks, each with $10^9$ CFU/day of LR.
Four mice not treated with CU1 were used as the control.

The expression of CFTR and NHE3 was measured by immunohistochemistry on colonocytes obtained from mice treated with CU1 and from control mice, as described below.

Immediately after sacrifice of the mice, samples of the proximal colon (1 cm long) were washed with 0.9% NaCl solution, fixed in a buffer solution at 4% of formaldehyde (6 h) and immersed for 24 h in a 30% sucrose solution at 4° C.

The samples were fixed in Tissue Tek medium (Euromedex, Souffelweyersheim, France) and frozen in isopentane at −45° C. Cryostat sections were post-fixed with acetone (10 minutes, −20° C.) and hydrated in phosphate-buffered saline (PBS)—milk solution. After incubation in a blocking solution (PBS with 0.25% of Triton X-100 containing 0.1% of bovine serum albumin (BSA)), the sections were incubated overnight at 4° C. with a rabbit anti-mouse CFTR (1/100), anti-mouse NHE3 (1/200) or anti-mouse TLR4 (1/100) polyclonal antibody (Abcam, Cambridge, UK). The sections were then incubated for 1 h at room temperature with an FITC-labeled donkey anti-rabbit antibody (1/2000, Uptima, Montluçon, France). The sections were then mounted in the "Vectashield HardSet mounting medium" (Abcys, Les Ulis, France) and were examined under a Nikon 90i fluorescence microscope (Nikon, Champigny-sur-Marne, France). Fluorescence intensity/$\mu m^2$ of the immunolabeling was measured with the Nis-Elements Ar software (Nikon). The analyses were carried out on five sections from a group of 4 mice.

Results

Figure 1:
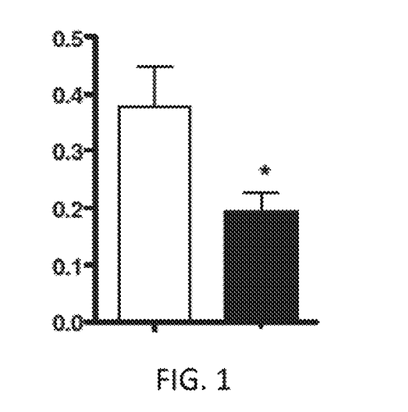
FIG. 1. Effect of treatment with the strain *Bacillus subtilis* CU1 on colonic expression of the CFTR protein. Fluorescence intensity/$\mu m^2$ is given for the control (in white) and after treatment with CU1 (in black). *$p<0.005$.
Figure 2:
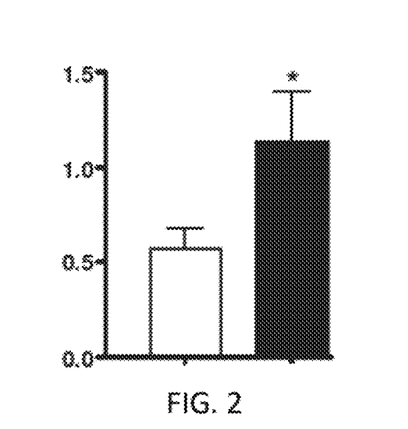
FIG. 2. Effect of treatment with the strain *Bacillus subtilis* CU1 on colonic expression of the NHE3 protein. Fluorescence intensity/$\mu m^2$ is given for the control (in white) and after treatment with CU1 (in black). *$p<0.005$.

Among the probiotic strains tested, only the CU1 strain of *Bacillus subtilis* was found to have an effect on expression of the two transporters CFTR and NHE3 that are involved in the movements of water through the colonic mucosa. In fact, as shown in FIG. 1, treatment of the mice for two weeks with the strain of *Bacillus subtilis* CU1 led to a significant reduction in expression of CFTR on the apical pole of the colonocytes in the colon of healthy mice. As shown in FIG. 2, treatment of the mice for 2 weeks with the strain of *Bacillus subtilis* CU1 led to a significant increase in expression of NHE3 on the apical pole of the colonocytes in the colon of healthy mice.

Figure 3:
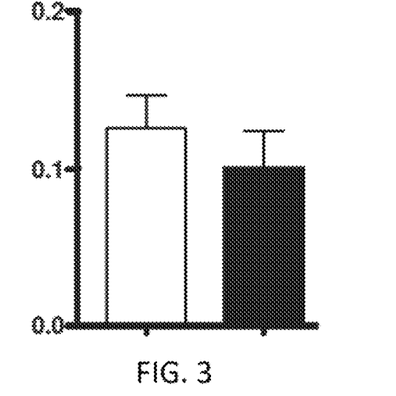
FIG. 3. Absence of effect of treatment with the strain *Lactobacillus plantarum* on colonic expression of the CFTR protein. Fluorescence intensity/$\mu m^2$ is given for the control (in white) and after treatment with LR (in black). *$p<0.005$.
Figure 4:
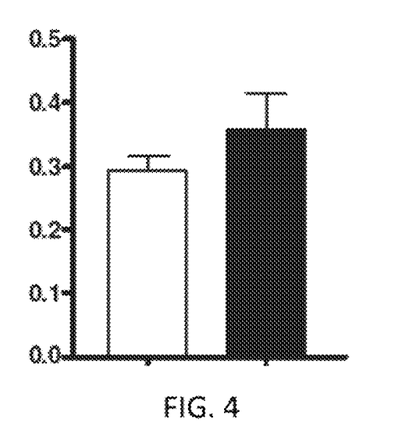
FIG. 4. Absence of effect of treatment with the strain *Lactobacillus plantarum* on colonic expression of the NHE3 protein. Fluorescence intensity/$\mu m^2$ is given for the control (in white) and after treatment with LR (in black). *$p<0.005$.

In contrast, as shown in FIGS. 3 and 4, treatment with the strain of *L. plantarum* did not significantly alter expression of CFTR or of NHE3.

Example 2: Use of the Probiotic Strain CU1 in the Prevention and/or Treatment of Diarrhea Material and Methods Model of LPS-Induced Diarrhea $10^9$ CFU/day/animal of the probiotic strain to be evaluated were administered via the intragastric route to male DBA/2 mice for 14 days.

The mice in the control group (12 mice) were then treated with 200 □L of water administered intravenously and the mice in the test group (12 mice) received an administration of lipopolysaccharide (LPS) of *Salmonella enteriditis* (Sigma, Saint Quentin Fallavier, France) intravenously at a dose of 15 mg/kg, to induce diarrhea. The mice were placed in individual cages with the floor covered with a sheet of aluminum to allow collection of feces every 30 minutes for 120 minutes after injection of LPS. The fecal material collected was weighed and heated at 100° C. for 24 h and weighed again. The difference between the wet mass of the fecal material (before heating) and the dry mass corresponds to the excretion of water. The diarrhea was evaluated relative to the total water excretion after administration of LPS.

Model of Diarrhea Induced by Castor Oil $10^9$ CFU/day/animal of the probiotic strain to be evaluated were administered by the intragastric route to male NMRI mice for 14 days.

The mice in the control group (12 mice) were treated with 200 µL of water administered by the intragastric route. 200 µL of castor oil (Sigma) was administered by the intragastric route to the male NMRI mice in the "test" group (12 mice), to induce diarrhea. The mice were placed in individual cages with the floor covered with a sheet of aluminum to allow collection of feces every 30 minutes for 180 minutes after administration of the castor oil. The fecal material collected was weighed and heated at 100° C. for 24 h and weighed again. The difference between the wet mass of the fecal material (before heating) and the dry mass corresponds to the excretion of water. The diarrhea was evaluated relative to the total water excretion after administration of the castor oil.

Model of Diarrhea Induced by an Antibiotic

An animal model of diarrhea induced by antibiotics was set up using a reduced number of antibiotics (based on the work by Chen et al., 2008, Gastroenterology, 135(6): 1984-92). Administration of antibiotics induces a dysbiosis (imbalance) of the flora as well as an immune response and a change in the number of mucus-producing cells of the mouse intestine. Antibiotic treatment can notably induce the appearance of *Clostridium difficile*.

Preventive treatment with the CU1 strain was tested in this model at a rate of $10^9$ CFU/day/animal for 14 days and 18 days on groups of 5 mice. After 7 days of administration of the CU1 strain, a mixture of 5 antibiotics was administered in the drinking water for 3 days, then on the next day the mice treated with the antibiotics received an intraperitoneal injection of clindamycin. The effet of the treatments was observed on days 14 and 18 following the start of the experiment. The mice treated with the CU1 strain received the strain throughout the test.

Results

The strain of *Bacillus subtilis* CU1 was tested in various models of diarrhea in mice.

Anti-Diarrhea Properties of the Strain of *Bacillus subtilis* CU1

Figure 5:
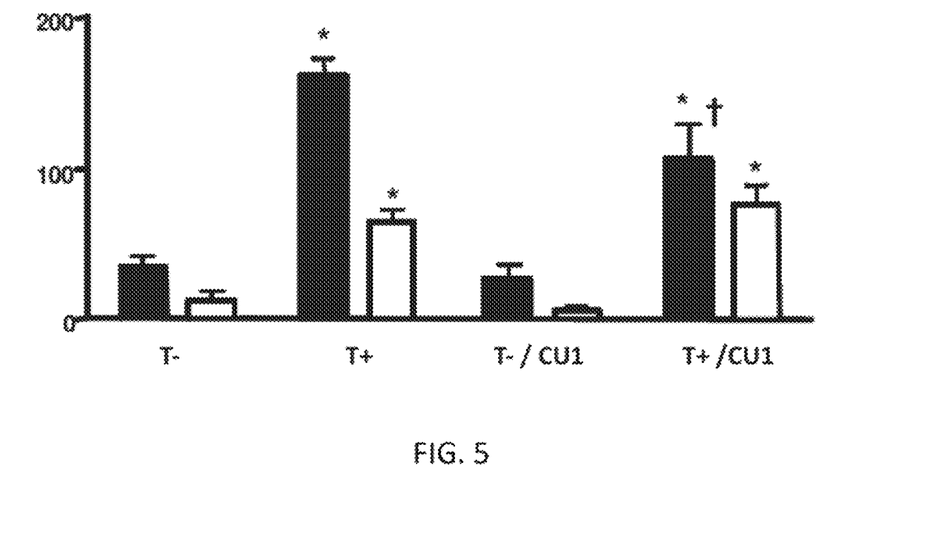
FIG. 5. Water excreted (in mg) in the feces in 60 minutes (in black) and between 60 and 120 minutes (in white) after intravenous administration of LPS (15 mg/kg) or of saline to mice (mean value±SEM, n=10-20). T−: mice not treated with CU1 that received an injection of saline; T+: mice not treated with CU1 that received an injection of LPS; T−/CU1: mice treated with CU1 that received an injection of saline, T+/CU1: mice treated with CU1 that received an injection of LPS. * $P<0.05$ vs T−; † $P<0.05$ vs T+.
Figure 6:
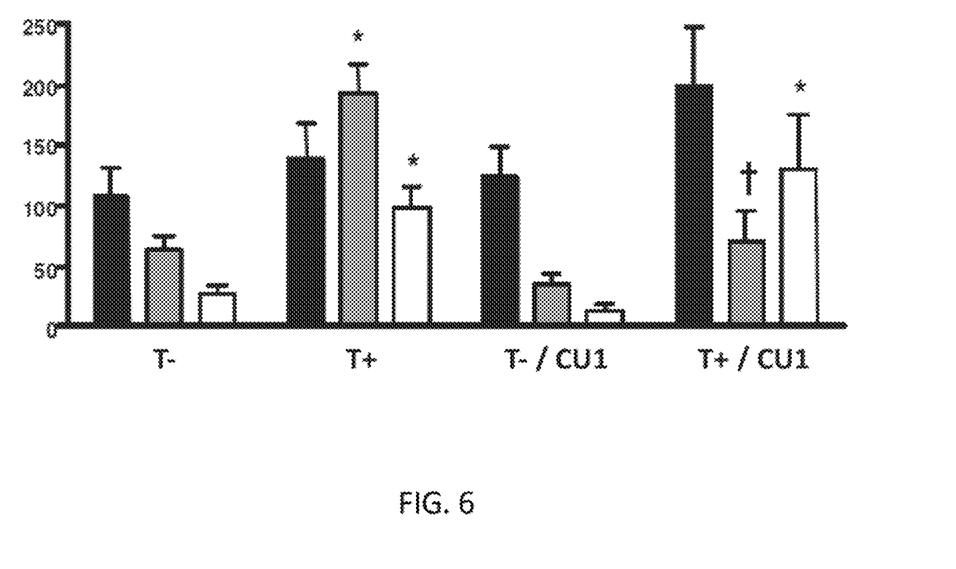
FIG. 6. Water excreted (in mg) in the feces in 60 minutes (in black), between 60 and 120 minutes (in gray) and between 120 and 180 minutes (in white) after intragastric administration of castor oil (200 □L) or of saline to mice (mean value±SEM, n=10-19). T−: mice not treated with CU1 that received an injection of saline; T+: mice not treated with CU1 that received an injection of castor oil; T−/CU1: mice treated with CU1 that received an injection of saline, T+/CU1: mice treated with CU1 that received an injection of castor oil. *$P<0.05$ vs T−; $P<0.05$ vs T+.

As shown in FIGS. 4 and 5, the CU1 strain significantly was found to significantly prevent diarrhea induced by LPS (FIG. 5) and by castor oil (FIG. 6).

In fact, administration of CU1 cells significantly decreased water excreted in the feces during the first hour after administration of LPS (in 4 tests, the decrease was 35%, 38%, 36% and 40%).

The administration of CU1 cells significantly decreased water excreted in the feces during the 2nd hour in the model of diarrhea induced by castor oil (in 3 tests, the decrease was 63%, 46%, 44%).

The CU1 strain also has a preventive effect on diarrhea induced by administration of antibiotics. This effect was observed after preventive treatment with CU1 cells: the mice then displayed a normalization of the intestinal microbiota and an improvement of the changes caused by the antibiotics at the level of the mucus-producing cells of the intestinal mucosa and on the macrophages.

Comparison with the Effect of Loperamide

A preventive treatment with the CU1 strain for 15 days was found to reduce diarrhea induced by LPS or castor oil with the same efficacy as loperamide, the reference antidiarrheic molecule, administered in a single dose (1 mg/kg) by the oral route one hour before diarrhea is initiated. Loperamide gives a 50% decrease in fecal excretion of water after LPS (40% for CU1) and 60% after castor oil (60% for CU1).

CONCLUSIONS

In vivo, the strain *Bacillus subtilis* CU1 can improve the absorption capacity of the colon in condition of fluid excess.

Additional studies showed that the strain *Bacillus subtilis* CU1:
- has no effect on the secretion/absorption capacities of the small intestine in the castor oil model and the LPS model,
- cancels the increase in paracellular permeability induced by LPS at the level of the wall of the colon, but not that induced by castor oil,
- reduces the short-circuit current induced by castor oil at the level of the wall of the colon, which suggests a reinforcement of the capacities of the colon for absorbing water in a laxative diarrhea situation induced by castor oil (and not in the baseline situation).

The strain *Bacillus subtilis* CU1 and the cells obtained by culture of this strain are thus useful for treating and/or preventing any type of diarrhea.

The invention claimed is:

1. A method of treating diarrhea in a patient comprising a step of administering, to the patient, an effective amount of a probiotic strain, wherein said probiotic strain is the strain of *Bacillus subtilis* CU1 deposited at the Collection Nationale de Cultures de Microorganismes (CNCM) on Oct. 25, 2001 under number I-2745.

2. The method according to claim 1, wherein the diarrhea is acute diarrhea or chronic diarrhea.

3. The method according to claim 1, wherein the diarrhea is diarrhea of infectious origin or diarrhea of noninfectious origin.

* * * * *